(12) United States Patent
Goethals et al.

(10) Patent No.: US 6,830,928 B1
(45) Date of Patent: Dec. 14, 2004

(54) PLANT MICROPROPAGATION AND GERMPLASM STORAGE

(75) Inventors: Koenraad Hilaire Maria Goethals, Ghent (BE); Mondher El Jaziri, Woluwe Saint Pierre (BE); Marc Charles Ernest Van Montagu, Brussels (BE)

(73) Assignees: Vlaam Interuniversitair Instituut Voor Biotechnologie, Zwijnearde (BE); Universite Libre de Bruxelles, Brussels (BE)

( * ) Notice: Subject to any disclaimer, the term of this patent is extended or adjusted under 35 U.S.C. 154(b) by 0 days.

(21) Appl. No.: 09/380,106

(22) PCT Filed: Feb. 19, 1998

(86) PCT No.: PCT/EP98/01117

§ 371 (c)(1),
(2), (4) Date: Nov. 24, 1999

(87) PCT Pub. No.: WO98/36635

PCT Pub. Date: Aug. 27, 1998

(30) Foreign Application Priority Data

Feb. 21, 1997 (EP) ............................................ 97200513
Mar. 10, 1997 (EP) ............................................ 97200701

(51) Int. Cl.⁷ .............................. C12N 5/00; C12N 5/02
(52) U.S. Cl. ...................................................... 435/420
(58) Field of Search ........................................ 435/420

(56) References Cited

PUBLICATIONS

Etude preliminaire des modifications induites chez le pois express Alaska par le corynebacterium fascians Rev Gen Bot 72:21–53 Roussaux M.J. 1965.*
Bhojwani SS. et al. Plant Tissue Culture Theory and practice Studies in Plant Science, 5.*
PCR amplification of the fas–1 gene for the detection of virulent strains of Rhodococcus fascians. Stange et. Plant pathology 1996 45 407–417.*

Principles of Plant Biotechnology Mantell et al. 1985.*
Danny Vereecke et al., *Patterns of phenolic compounds in leafy galls of tabacco,* PLANTA, vol. 201, No. 3, 1997, pp. 342–348.
Martin Crespi et al., *Fasciation induction by the phytopathogen Rhodococcus fascians depends upon a linear plasmid encoding a cytokinin synthase gene,* The EMBO Journal., vol. 11, No. 3, 1992, pp. 795–804.
E. Balazs et al., *Altered Levels of Indoleacetic Acid and Cytokinin in Geranium Stems Infected with Corynebacterium fascians,* ACTA Phytopathologica Academiae Scentarum Hungaricae, vol. 9, No. 3–4, 1974, pp. 287–292.

* cited by examiner

*Primary Examiner*—Anne Marie Grunberg
*Assistant Examiner*—Annette H Para
(74) *Attorney, Agent, or Firm*—Knobbe, Martens, Olson & Bear, LLP

(57) ABSTRACT

The present invention relates to a method for the in vitro preparation of starting materials for micropropagation and/or storage of germplasm, comprising the steps of contacting plant material with a microorganism that induces fasciation and/or one or more fasciation-inducing factors derived from the microorganism or derived from the infected and/or fasciated tissue; developing leafy galls or shoot outgrowths on the plant material; and isolating the leafy galls or shoot outgrowths as the starting materials. This method may be used for the in vitro micropropagation of plants, which further comprises the steps of eliminating or inactivating the microorganism that induces fasciation and/or the one or more fasciation-related factors derived from the microorganism or derived from the infected and/or fasciated tissue; culturing the leafy gall or shoot outgrowths in or on one or more suitable culture media to allow shoot and root development for obtaining plantlets; and transferring the plantlets thus obtained, optionally after acclimatization, to conventional growing conditions to obtain regenerated plants. The method may also be used for the preservation of plants or germplasm, which is further characterized by the step of storing the leafy galls or shoot outgrowths under growth limiting conditions.

6 Claims, 1 Drawing Sheet

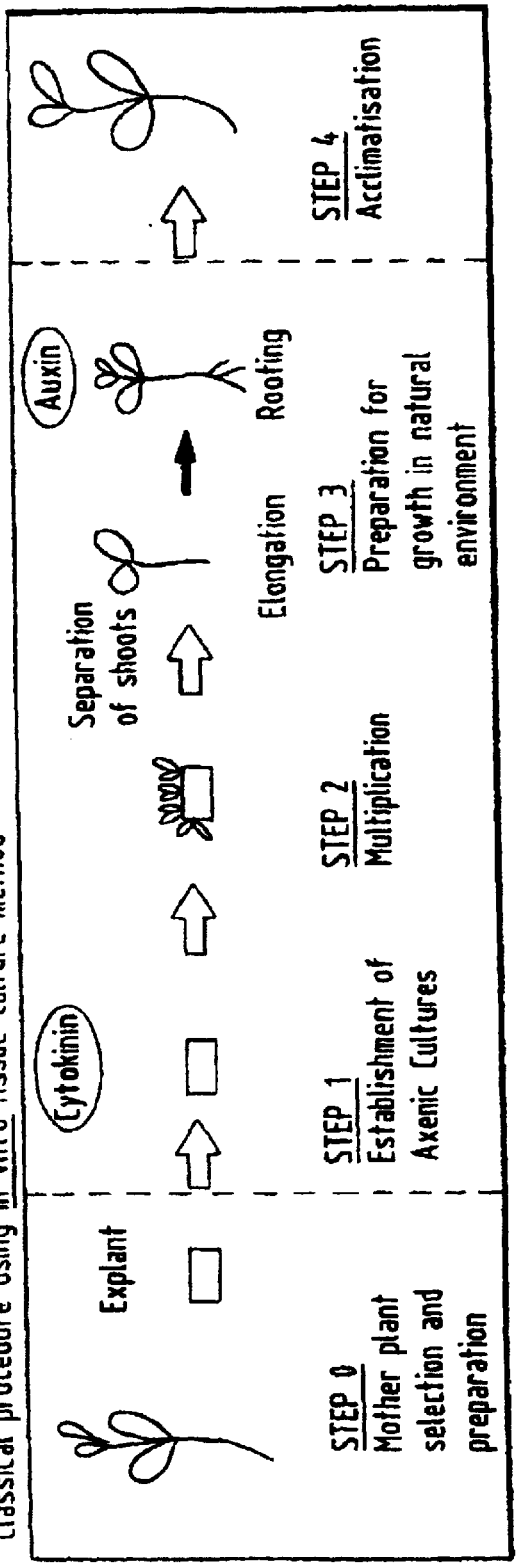
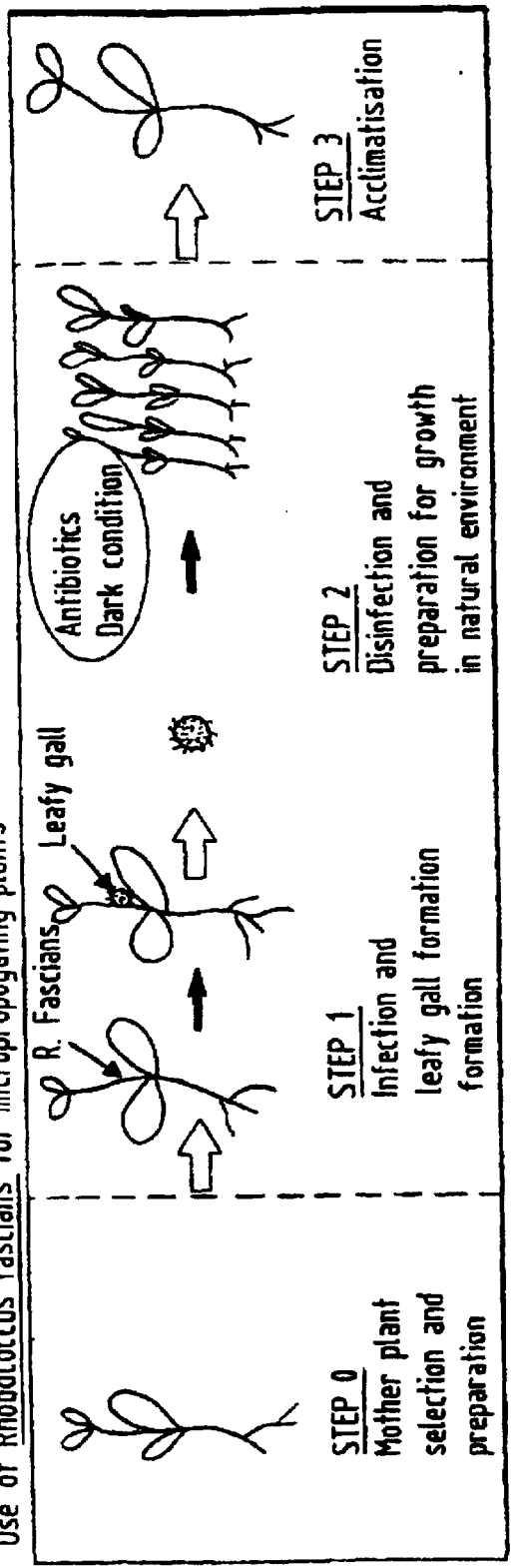

PLANT MICROPROPAGATION AND GERMPLASM STORAGE

This is U.S. National Phase under 35 U.S.C. §371 of International Application PCT/EP98/01117, filed Feb. 19, 1998, which claims priority to EP 97200701.7, filed Mar. 10, 1997 and EP. 97200513.6, filed Feb. 21, 1997.

The present invention relates to new methods of plant micropropagation and germplasm storage.

Plants can be propagated through their two developmental life cycles: the sexual or the asexual (or vegetative). In the vegetative (asexual) cycle the unique characteristics of any individual plant selected for propagation are usually perpetuated. In most cases, each new plant produced by this method may be considered to be an extension of the somatic cell line of one individual. Methods available for propagating plants in vitro (micro-propagation) are largely an extension of those already developed for conventional propagation (macro-propagation).

The methods that are theoretically available for propagating plants in vitro are essentially based on the multiplication of shoots from axillary buds, on the formation of adventitious shoots and on the formation of somatic embryos. These processes are initiated either directly from the original explant or indirectly from unorganised cells such as in callus or cell suspension cultures.

In practice most micropropagated plants are produced at present by the multiplication of shoots from axillary buds. Nevertheless, somatic embryos, shoots and/or plantlets do not always originate in a single way. For example, in shoot cultures, besides axillary shoots, there are sometimes adventitious shoots formed directly on existing leave or stem explants and/or shoots arising indirectly from callus at the base of the explant.

Considering these observations, somaclonal variation is frequently observed among the regenerated plants even through multiplication of shoots from axillary buds which is considered as the most stable source for plant micropropagation. In such mixed cultures, shoots arising indirectly from callus are not desirable because of the somaclonal variation. This is particularly important when the method is applied in a large-scale programme (industrial scale). In order to reduce this genetic/epigenetic variation, standardization of the cellular origin for the regenerated new shoots is therefore essential.

A second limitation of the method of axillary shoot production is associated with the use of exogenous phytohormones for plant micro-propagation purposes. The growth and proliferation of axillary shoots in shoot cultures is usually promoted by incorporating growth regulators into the culture medium. Depending on the plant species, usually cytokinins and auxins in appropriate combinations and concentrations are used. Such treatments effectively remove the dominance of apical meristems so that axillary shoots are produced. These shoots are used as miniature cuttings for plant multiplication.

The cytokinin growth regulators added to shoot culture media to promote axillary shoot growth, usually inhibit root formation. Therefore, single shoots must be moved to a different medium for rooting in vitro (generally medium containing auxins) before being transferred as juvenile plantlets to the external environment. The axillary shoot production thus requires a sequence of steps.

Nowadays, there is an increased tendency to consider that exogenous applied synthetic cytokinin, which is generally too high, may cause many abnormal features (side effects) such as production of small shoots which typically fail to elongate, induction of unusual leave shapes and particularly the tendency of the regenerated shoots to become vitrified.

In addition, high concentrations of usual cytokinins generally inhibit or considerably delay root formation and also prevent root growth and the promoting effects of auxins on root initiation. In this respect. frequently more than one subculture to a cytokinin-free medium may be required until the level of cytokinin within the tissues has been sufficiently reduced followed by a transfer of the shoots to a rooting medium.

Considering these aspects it is furthermore impossible to propagate particular plant species which are sensitive to such hormonal treatments.

It is thus the object of the present invention to provide an alternative micropropagation method with which the above identified drawbacks of the known methods are obviated.

According to the invention it has surprisingly been found that leafy galls, which are produced on dicotyledonous plants by infection with particular micro-organisms or by treatment with substances produced by these micro-organisms or derived from the infected and/or fasciated tissue (so-called fasciation), and which consist of multiple meristematic centers and shoot primordia that are suppressed for elongation, are an excellent starting point for micropropagation. In a gall no apical dominance phenomena are evident and the formation of numerous primordia is derepressed by the infection process. The gall is in fact a large mass of shoot primordia that are covered with leaves and that are infected by the micro-organism. In leafy galls specific metabolites are present that are involved in the establishment and the maintenance of the leafy gall structure.

In monocotyledonous plants the structures that arise upon contact with or infection by fasciation-inducing micro-organisms or substances have a different morphology than the above described leafy galls that are formed in dicotyledonous plant material. Infection either results in deformation of bulbs and/or the formation of several elongated shoots. These monocot elongated shoot structures are useful in the method of the invention and will be further identified as "shoot outgrows", whereas the dicot structures are called "leafy galls".

Apart form the morphogenetic aspects, a gall represents a center of elongation inhibition where the bacterium suppresses the outgrowth of the primordia in the gall. This phenomenon is translated in the apparent lack of apical dominance that would be exerted by one of the primordia and would lead to the outgrowth of distinct shoot primordia from the gall tissues. As such, each gall can be considered as a highly condensed plant where the amplified production of primordia and meristems—apical as well as axillary—are confined to one compact region through the suppression of both the elongation processes and apical dominance.

Furthermore, it was found according to the invention that due to the fact that the galls consist of large numbers of shoot primordia confined to a compact and small structure, they are also a very suitable material for germplasm storage.

Starting from these two observations the present invention now provides for a method for the in vitro preparation of starting materials for micropropagation and/or storage of germplasm, comprising the steps of:

a) contacting plant material with a micro-organism that induces fasciation and/or one or more fasciation-inducing factors derived from the micro-organism, or derived from the infected and/or fasciated tissue;

b) developing leafy galls or shoot outgrows on the plant material; and c) isolating the leafy galls or shoot outgrows as the starting materials.

This method of the invention may then be incorporated in a method of micropropagation or a method of germplasm storage, respectively. A method for the in vitro micropropagation of plants comprises the above described method for the preparation of starting material, further characterized by the steps of d) eliminating or inactivating the micro-organism that induces fasciation and/or the one or more fasciation-related factors derived from the micro-organism or derived from the infected and/or fasciated tissue;

e) culturing the leafy gall or shoot outgrows in or on one or more suitable culture media to allow further shoot and root development for obtaining plantlets, and f) transferring the plantlets thus obtained, optionally after acclimatisation, to conventional growing conditions to obtain regenerated plants.

A method for the preservation of plants or germplasm comprises the method for the preparation of starting material, further characterized by the step of storing the leafy galls or shoot outgrows under growth limiting conditions. The growth limiting conditions may comprise low temperatures of about 4° C. or cryo-conserving conditions, such as storage in liquid nitrogen.

Both methods are not only applicable on angiosperms, but also on gymnosperms.

In a preferred embodiment of the invention the fasciation inducing micro-organism is the Gram positive bacterium *Rhodococcus fascians* (Tilford) (Goodfellow M. & Cross, T., "Classification", published: Goodfellow. Modarski & Williams ed., The Biology of Actinomycetes, Academic Press London, p. 7–64 (1984)). (Effective publication Goodfellow M., "Reclassification of Corynebacterium fascians (Tilford, Dowson) in the genus Rhodococcus, as *Rhodococcus fasc.* comb. nov." System. Appl. Microbiol. 5, 225–229 (1984), previously known as *Phytomonas fascians* Tilford, J., Agric. Res. 53, 383–394 (1936); or *Corynebacterium fascians* (Tilford) Dowson, W. J., Trans. Brit. Myc. Soc. 25, 311–314 (1942)). *Rhodococcus fascians* is a Nocardioform Actinomycete that infects a whole range of both dicotyledonous and monocotyledonous plants.

The range of plants that can be infected by *R. fascians* is very broad with different species belonging to numerous plant families, such as Brassicaceae, Salicaceae, Compositae, Solanaceae, Scrophulariaceae, Liliaceae, Papaveraceae, Gramineae and Fabaceae.

Infection of an intact plant can for example be achieved by vacuum infiltration of plants with suspensions of the bacteria, application of a dense bacterial culture sample to a wound surface or, less efficiently, by simply applying bacteria in either the growth substrate of the plants or on the surface of intact plants. Also explants, such as leaf discs, organs, tissue fragments, and seedlings, seeds, embryos, isolated cells and protoplasts can be successfully infected. giving rise to leafy galls or shoot outgrows. Furthermore, *R. fascians* infected cell cultures and callus tissues react in a similar fashion.

The role of *R. fascians* in the phenomenon of suppression of elongation and apical dominance can be exemplified by killing of the bacteria in the gall through a treatment with bactericidal agents such as Carbenicillin, Triacellin and Claforan. Growth of detached galls on hormone free plant media with the addition of bactericidal compounds to an end concentration of 500 mg/L, results in the release of the amplified primordia from the bacterial suppression. ensuing in the outgrowth of numerous independent shoots from the gall tissues that will produce root tissues. The rooting can be facilitated by treating the galls in the dark where the release of the shoots is accompanied by etiolation, producing masses of elongated sprouts. Each shoot can be transferred to another medium resulting in the production of a fertile plant clone.

These new micropropagation and germplasm storage methods are widely applicable and may for example be used for trees, crops, medicinal and aromatic plants. The methods are also suitable for biochemical or genetic selection purposes.

Instead of using the micro-organism as a whole one or more factors derived from the micro-organism or infected and/or fasciated tissue may be used. These factors are capable of inducing the formation of leafy galls in dicotyledonous plants and shoot outgrows in monocotyledonous plants. The factors may for example be gene products of the genes involved in fasciation, or the molecules produced by these gene products.

In the *R. fascians* strain D188, the property to induce fasciation is correlated with the presence of a ±200 kb large linear plasmid, pFiD188, that carries several loci (e.g. fas, att and hyp) involved in leafy gall formation. The present inventors have found that mutations in the fas locus render the bacteria non-pathogenic. A mutation in the att locus provokes attenuated fasciation resulting in smaller leafy galls that are formed more slowly. Finally, a mutation in the hyp locus results in hyper-fasciation, leading to the formation of larger galls compared to wild type.

Apart from pFiD188 encoded genes, also chromosomal genes in the bacterium are involved in the infection process for instance by influencing the endophytic/epiphytic survival of *R. fascians*.

Evidently, gall formation results from the modulation of the regular hormone balance in the infected plant tissues. Although the fasciation symptoms superficially resemble effects caused by the application of different doses of several cytokinins, they are nevertheless clearly discriminated from the latter by the presence of non-elongating primordia and the absence of abundantly developing shoots. Early reports where galling was correlated with the presence of different cytokinins in the growth medium of *R. fascians* have recently been questioned by opposing results. This is further substantiated by the present inventors by their finding of the presence of cytokinins in the growth media of a non-fasciating strain D188-5 (Crespi et al., EMBO J. 11, 795–804 (1992)) cured for pFiD188.

Although early results hinted at the presence of an adenosine monophosphate isopentenyl transferase (ipt) homologous gene in the fas locus on pFiD188 that would be involved in the biosynthesis of cytokinins (Crespi et al., 1992, supra), the present results question the unique involvement of the ipt homologue in the biosynthesis of regular cytokinins like isopentenyl adenine or zeatin. Instead, the fas locus is involved in the production and secretion of one or more isopentenylated molecules that affect the plants hormone levels. This was confirmed by the isolation and preliminary chemical analysis of one fas dependent products and fits with the overall low amino acid identity between the fas encoded ipt gene product and regular isopentenyl transferase proteins. Apart from the ipt related gene, the fas locus encodes several genes that, on the basis of sequence homology studies, are implicated in cytochrome P450 dependent oxygenation and S-Adenosyl Methionine dependent methylation processes of, conceivably, the fas product.

High expression of the fas locus in the bacterium—as measured by translational GUS fusion assays—is strictly controlled and can only be consistently achieved in batch cultures using a defused induction medium, such as Minimal A-medium (obtainable by adding 20.5 ml 0.1M citrate and 29.5 ml 0.1M Na-citrate to 450 ml destilled water and adding after autoclaving and cooling 500 µl 1% (w/v) thiamine, 1.25 ml $MgSo_4$ and 1.25 ml 40% $NH_4SO_4$) and only in the presence of either gall extracts or histidine in combination with particular carbon sources such as pyruvate and succinate. Plant extracts cannot induce fas gene expression, but gall extracts contain a specific inducer molecule. This inducer molecule is present in all gall tissues formed on a whole range of different plants and is able to induce expression in minimal concentrations. Furthermore, production of this molecule was shown in tobacco BY-2 cell cultures confronted with R. fascians wild type cells while this was not the case for non-infected plant cell cultures or pure bacterial cultures.

The fas expression is mainly regulated at the post-transcriptional level, indirectly through the activity of the fasR gene that encodes an AraC type transcriptional activator and possibly directly through the hyp locus that carries a gene encoding an RNA-helicase.

Confrontation of BY-2 tobacco cell culture synchronized for mitosis using aphidicolin with fas induced D188 cells resulted in a marked increase of the number of tobacco cells that enter the first round of mitosis upon relieve of the mitosis block. This effect is absent when the tobacco cell culture is confronted with the non-fasciating strain D188-5 or with fas mutant strains.

Classical cytokinin-bioassays using extracts of R. fascians D188 and D188-5 grown for fas induction proved difficult to interpret due to the presence of high background levels of contaminating cytokinins in both tested extracts. From D188 cultures, induced for fas expression, a fas dependent metabolite was isolated.

The att locus comprises a 20 kb region of pFiD188, linked to the fas locus. Sequencing showed the presence of several genes that are involved in the synthesis and secretion of a complex molecule of unknown structure. Apart from genes involved in the synthesis of arginine, the locus carries genes implicated in the biosynthesis and modification of fatty acid related molecules and a gene related to export protein genes.

Expression of the att locus is partially co-regulated with the fas locus; induction of GUS fusions is only visible in defined media in the presence of gall extracts or of histidine in combination with particular carbon sources and depends on the activity of the fasR gene. However, an independent regulation through an att specific regulatory gene, attR, is postulated here whereby the expression of the attR gene is itself enhanced by the fasR gene in response to plant extracts.

Using $^{14}C$-labelled arginine or acetate, in either case the induced accumulation in the growth medium of R. fascians D188 of the same $^{14}C$-labelled, att dependent compounds was evident using thin layer chromatography, proving the incorporation of both tested substrates in complex, secreted compounds. These were isolated through High Pressure Liquid Chromatography for chemical analysis and bioassaying using BY-2 tobacco cell cultures. As an example; a molecule with a molecular weight of 681 dalton was isolated.

The products of the att locus are probably involved in the formation of leafy galls in combination with the fas locus as a mutant in the locus is strongly retarded in the galling process. It is also conceivable that the att and fas loci cooperate in the biosynthesis and secretion of a single type of molecules that provoke fasciation.

Apart from the fas and att loci, still other loci on pFiD188 are involved in the formation of leafy galls. The hyp locus probably negatively controls expression of the as and att expression through RNA helicase activity on the mRNA. Further downstream of the fas locus another locus has been isolated that is essential for fasciation and sequencing of which showed the presence of oligopeptide synthetic genes.

Molecular analysis of the gene expression in infected tobacco plants using differential display techniques showed the induction of different genes showing homology to genes involved in the metabolism of gibberellins and steroids as well as the repression of a gene showing homology to oligopeptide receptor proteins. These results strongly suggest an influence of the infecting bacteria and their products on the existing balances of different plant growth factors, resulting in the induction of meristem and primordium formation.

The formation of a leafy gall by R. fascians is thus a complex process with different levels of signalling between both partners. The expression of the bacterial fasciation genes located on the linear plasmid is prone to a complex regulation that ultimately implies the involvement of a gall specific metabolite in the fasR dependent induction of the att and fas genes. Once the fas and att genes are optimally expressed, metabolites are produced and secreted in the plant that disturb and/or redirect the hormone household of the plant tissues. The fas and att derived factor(s) are implicated in the enhancement of plant cell divisions and are crucial for the activation of the gall formation. Molecular data suggest the involvement of gibberellins, steroid type molecules and/or possibly oligopeptides of the plant. This unique response of the plant to infection confers the particular properties of R. fascians and its derived products in altering the developmental programming of the plant in some hitherto non-described way. It further discriminates the leafy gall syndrome from other neoplastic pathologies like the Agrobacterium tumefaciens induced crown gall formation and the Pseudomonas savastanoi induced galling of Oleander species.

In summary, it has now been found that a gall constitutes several meristems and primordia the formation of which is correlated with the fas product, the att products, or a combination of both and possibly other products the synthesis of which is determined by different loci on pFiD188 or on the bacterial chromosome. The end result is a local activation and deregulation of primordium and meristem formation that results in dense tissues—the gall—that is ultimately covered with leaflets. Morphological analysis of these galls suggest an organised spatial distribution of the primordia that are covered with leaflets, both according to the fundamental rules of phyllotaxis.

Based on the experimental information provided here it became possible to identify a complex of factors that can be used to induce fasciation independently from the bacteria as a whole. This complex of factors comprises at least the fas products and/or the att products and in addition other gene products encoded by the pFiD188 plasmid.

The unique property of R. fascians to amplify shoot primordium formation through the modulation of specific hormone balances in a broad spectrum of plants is useful for the establishment of a regeneration program for a diverse range of plants as will be illustrated in the following examples. Infection of plants with R. facians leads to the local amplification of shoot primordia, combined with a suppression of further shoot growth and development. Upon amplification, primordia can be released from the suppressive effects of R. fascians by killing of the bacteria. This can be achieved by detaching galls and growing them on media with doses of bactericides like penicillin's. Any other treatment of the galls that will kill the inciting bacteria without harming the plant tissue can be envisioned here.

As a result, from the gall tissues shoots will sprout that can be detached and that will form roots, ultimately giving rise to normal, regenerated plants. This effect is even more dramatic when the galls are treated in the dark, where the release of shoots is accompanied by etiolation, producing masses of elongated sprouts that can be propagated to a normal plant.

This technique has been successfully applied to leafy galls on *Nicotiana tabacum, Papaver somniferum, Artemisia annua, Viqna unguiculata, Atropa belladona, Sesbania rostrata* and *Digitalis lanata*.

The FIGURE is an overview showing the steps required for micropropagation using either classical procedure or *Rhodococcus fascians*.

This invention as described here will be further illustrated in the following examples.

EXAMPLES

Example 1

Regeneration of Pants from Leafy Galls of Various Plant Species-induced by *Rhodococcus fascians*

1. General Method

The following method is applicable to plant species in general. In these examples the plant species *Nicotiana tabacum, Papaver somniferum, Artemisia annua, Viqna unguiculata, Atropa belladona, Sesbania rostrata* and *Digitalis lanata* were used.

1.1. Bacterial Strain

Rhodoccocus fascians strain D188 or other virulent strains are cultured in solid or liquid conventional bacteria medium or a recommended one containing: Glucose (10 g/l), Yeast extract (5 g/l), Peptone (5 g/l), Agar (15 g/l), distilled water 1l, the pH adjusted to 7.0. The cultures are then incubated in the dark at 25° C.

1.2. Plant Material

Selected plant species are used for the propagation purposes. After surface desinfection of the explants (for example: cutting consisting of stem internode fragments with axillary buds) using appropriate reagents known in the art, the explant is transferred to in vitro culture condition using conventional tissue culture medium such as the well-known basal Murashige and Skoog medium (Physiol. Plant. 15, 473–497) or Gamborg medium (Gamborg, O. L. et al., Ex. Cell. Res. 50, 151 (1986)).

1.3. Infection Procedure

The axenic explant is directly infected with the fast growing bacteria or infected under vacuum. All other method of infection which make close contact of the bacteria and the plant tissue or cells are also suitable.

In case of *Sesbania rostrata*, cotyledonous explants were used for direct infection with *Rhodococcus fascians*. Preferably wounded cotyledons were used for this infection in order to obtain a more efficient infection.

1.4. Incubation of the Infected Explant

Containers containing the infected plant material are incubated in the room culture at 23° C. Depending on the plant species, leafy galls came to be visible after 3–4 weeks of incubation.

2. Regeneration of Plants Leafy Galls Structure 2.1. General Procedure

The leafy galls are first isolated from the original explants. Then they are subcultured in a hormone-free conventional plant tissue culture medium additionated with bactericide reagent such as Claforan at final concentration of 500 mg/l. The cultures are preferably incubated in the dark at appropriate temperature (depending on the plant species, for example 19° C. for Papaveraceae species; 23° C. for Solanacaea species).

2.2. Results

The dark condition combined with the antibiotic treatment improve the shoot elongation. The etiolated shoots thus obtained are then subcultured in a hormone-free culture medium and incubated in light condition. The light intensity as well as the temperature of incubation are selected according to the specific requirement of each plant species under investigation. After several days of cultures, spontaneous root appeared, and thus plantlet are recovered.

Using the described method and in the case of *Digitalis lanata*, an average of 60 new regenerated shoots/explant are obtained instead of 12 new regenerated shoots using the classical micropropagation method (using exogenous cytokinins).

Using common method for acclimatization, these new regenerated plantlets awe successfully transferred to the green house.

Quantitative and qualitative analysis of cardenolides in the new regenerated plants showed a distribution quite similar to that of the mother plant. In addition the morphological traits of these new regenerated plants are similar to those of the mother plant, indicating a reduced variability as compared to the classical micropropagation technique.

Example 2

Germplasm Storage

1. Short-term Conservation

The leafy galls containing the bacteria are isolated from the original explant then subcultured in a conventional plant tissue culture medium with reduced sugar concentration (15 g/l of sucrose). After one week of culture at 20° C., the culture containers are transferred to 4° C. under dark condition. In such conditions the capability of the shoots to develop (after bactericide treatment) is maintained for 1–2 years.

2. Long Term Conservation

The well established procedure for cryoconservation using liquid nitrogen is also convenient for the leafy gall structure (George. E. F., in: Plant Propagation by Tissue Culture, Part I, George Edwin F. (Ed.), Exegetics Ltd., Edington, Wilts, England, pp. 163–181 (1993)).

What is claimed is:

1. A method for micropropagation of plants, comprising the steps of:
   (a) contacting plant material with a micro-organism that induces fasciation;
   (b) developing leafy galls or shoot outgrowths on the plant material;
   (c) isolating the leafy galls or shoot outgrowths as a starting material for micropropagation of plants;
   (d) eliminating or inactivating the micro-organism that induces fasciation;
   (e) culturing the leafy gall or shoot outgrowths in or on one or more suitable culture media to allow shoot and root development for obtaining plantlets; and
   (f) transferring the plantlets thus obtained to conventional growing conditions to obtain regenerated plants, wherein the plant material is chosen from the group consisting of intact plants, leaf discs, organs, tissue fragments, seedlings, seeds, embryos, isolated cells, protoplasts, cell cultures and callus tissues.

2. A method of preservation of plants or germplasm storage comprising the steps of:
(a) contacting plant material with a micro-organism that induces fasciation;
(b) developing leafy galls or shoot outgrowths on the plant material;
(c) isolating the leafy galls or shoot outgrowths as a starting material for micropropagation of plants; and
(d) storing the leafy galls or shoot outgrowths under growth limiting conditions, further characterized in that said plant material is chosen from the group consisting of intact plants, leaf discs, organs, tissue fragments, seedlings, seeds, embryos, isolated cells, protoplasts, cell cultures and callus tissues.

3. The method of claim 1, wherein the fasciation-inducing micro-organism is *Rhodococcus fascians*.

4. The method of claim 1, wherein the plant material is material of species of families selected from the group consisting of: Brassicaceae, Salicaceae, Compositae, Solanaceae, Scrophulariaceae, Liliaceae, Papaveraceae, Gramineae and Fabaceae.

5. The method of claim 2 wherein the plantlets are acclimatized before conventional growing conditions to obtain regenerated plants.

6. The method of claim 2, wherein the fasciation-inducing micro-organism is *Rhodococcus fascians*.

* * * * *

UNITED STATES PATENT AND TRADEMARK OFFICE
CERTIFICATE OF CORRECTION

PATENT NO. : 6,830,928 B1
DATED : December 14, 2004
INVENTOR(S) : Goethals et al.

It is certified that error appears in the above-identified patent and that said Letters Patent is hereby corrected as shown below:

<u>Column 8,</u>
Line 5, delete "inactivating the micro-organism" and insert -- inactivating the microorganism --.
Line 52, delete "with a micro-organism" and insert -- with a microorganism --.

<u>Column 9,</u>
Line 58, delete "with a micro-organism" and insert -- with a microorganism --.

<u>Column 10,</u>
Lines 2 and 14, delete "micro-organism is" and insert -- microorganism is --.

Signed and Sealed this

Eleventh Day of April, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,830,928 B1 | Page 1 of 1 |
| APPLICATION NO. | : 09/380106 | |
| DATED | : December 14, 2004 | |
| INVENTOR(S) | : Goethals et al. | |

It is certified that error appears in the above-identified patent and that said Letters Patent is hereby corrected as shown below:

<u>Column 8,</u>
Line 5, delete "inactivating the micro-organism" and insert -- inactivating the microorganism --.
Line 52, delete "with a micro-organism" and insert -- with a microorganism --.

<u>Column 9,</u>
Line 5, delete "with a micro-organism" and insert -- with a microorganism --.

<u>Column 10,</u>
Lines 2 and 14, delete "micro-organism is" and insert -- microorganism is --.

This certificate supersedes Certificate of Correction issued April 11, 2006.

Signed and Sealed this

Second Day of October, 2007

JON W. DUDAS
*Director of the United States Patent and Trademark Office*